(12) United States Patent
Maurat et al.

(10) Patent No.: US 11,504,313 B2
(45) Date of Patent: Nov. 22, 2022

(54) COMPOSITION FOR AIR POLISHING

(71) Applicant: PRODUITS DENTAIRES PIERRE ROLLAND, Merignac (FR)

(72) Inventors: Vincent Maurat, Pessac (FR); Clemence Pigeron, Bordeaux (FR)

(73) Assignee: PRODUITS DENTAIRES PIERRE ROLLAND, Merignac (FR)

( * ) Notice: Subject to any disclaimer, the term of this patent is extended or adjusted under 35 U.S.C. 154(b) by 125 days.

(21) Appl. No.: 17/177,087

(22) Filed: Feb. 16, 2021

(65) Prior Publication Data
US 2021/0177711 A1 Jun. 17, 2021

Related U.S. Application Data

(63) Continuation of application No. 16/076,086, filed as application No. PCT/FR2017/050225 on Feb. 2, 2017, now Pat. No. 11,071,696.

(30) Foreign Application Priority Data

Feb. 8, 2016 (FR) ....................... 1650961

(51) Int. Cl.
| *A61K 8/21* | (2006.01) |
| *A61K 8/24* | (2006.01) |
| *A61K 8/25* | (2006.01) |
| *A61K 8/44* | (2006.01) |
| *A61K 8/90* | (2006.01) |
| *A61Q 11/00* | (2006.01) |

(52) U.S. Cl.
CPC .................. *A61K 8/21* (2013.01); *A61K 8/24* (2013.01); *A61K 8/25* (2013.01); *A61K 8/44* (2013.01); *A61K 8/90* (2013.01); *A61Q 11/00* (2013.01); *A61K 2800/28* (2013.01); *A61K 2800/412* (2013.01); *A61K 2800/43* (2013.01); *A61K 2800/884* (2013.01)

(58) Field of Classification Search
CPC . A61Q 11/00; A61K 8/24; A61K 8/25; A61K 8/44; A61K 8/21
USPC ....................................................... 424/489
See application file for complete search history.

(56) References Cited

U.S. PATENT DOCUMENTS

| 2,196,154 A | 4/1940 | Schulerud et al. |
| 4,623,536 A | 11/1986 | Winston et al. |
| 4,645,662 A | 2/1987 | Nakashima et al. |
| 5,885,555 A | 3/1999 | Sheehan |
| 6,106,811 A | 8/2000 | Gibbs |
| 6,126,444 A | 10/2000 | Horiguchi |
| 6,648,644 B1 | 11/2003 | Flemmig et al. |
| 2004/0202980 A1 | 10/2004 | Policicchio |
| 2006/0045851 A1 | 3/2006 | Fitzgerald et al. |
| 2010/0015252 A1* | 1/2010 | Speronello ............. A61Q 11/00 424/661 |
| 2015/0125814 A1 | 5/2015 | Haeberlein et al. |

FOREIGN PATENT DOCUMENTS

| CN | 103637927 A | 3/2014 |
| FR | 2572925 A1 | 5/1986 |
| GB | 2137494 A | 10/1984 |
| JP | H11244303 A | 9/1999 |
| JP | 2002538191 A | 11/2002 |
| KR | 101074880 B1 | 10/2011 |
| RU | 2003133989 A | 3/2005 |
| RU | 2264208 C2 | 11/2005 |
| WO | 2013191903 A1 | 12/2013 |

OTHER PUBLICATIONS

International Search Report from PCT Application No. PCT/FR2017/050225, dated Jun. 12, 2017.
"Anti-Inflammation and Whitening Tooth Powder," MINTEL, Shantou Kangwang Fine Chemicals, Aug. 2014, 4 Pages. http://www.gnpd.com.
"Tooth Powder," MINTEL, Lion Corporation, Jan. 2009, 3 Pages. http://www.gnpd.com.
"Tooth Stain Remover," MINTEL, Ngoc Mai Enterprise, Apr. 2004, 2 Pages. http://www.gnpd.com.

* cited by examiner

*Primary Examiner* — Walter E Webb
(74) *Attorney, Agent, or Firm* — Workman Nydegger

(57) ABSTRACT

A composition for air polishing the surface of hard dental tissue includes an abrasive first powder suitable for polishing hard dental tissue; a second powder of a gelling agent; and a third powder of a dental treatment agent.

13 Claims, 4 Drawing Sheets

COMPOSITION FOR AIR POLISHING

BACKGROUND OF THE INVENTION

The invention relates to a novel composition for air polishing the surface of hard dental tissue and to its use in an air polishing method.

Powders for dental air polishing are generally based on glycine, calcium carbonate, or sodium bicarbonate. Known powders include in particular a glycine-based powder developed by the supplier 3M ESPE and available under the reference "Clinpro Prophy Powder" for subgingival use, and a sodium bicarbonate-based powder sold by the supplier Satelec under the reference "Air-n-go Classic" for supragingival use.

Nevertheless, there exists a need to improve existing air polishing treatments so as to functionalize such treatments further without thereby leading to a significant lengthening of treatment time.

There exists in particular a need to have improved air polishing treatment available that also makes it possible to perform effective therapeutic action on the treated tooth without that leading to a significant lengthening of treatment time.

OBJECT AND SUMMARY OF THE INVENTION

To this end, in a first aspect, the invention provides a composition for air polishing the surface of hard dental tissue, the composition comprising at least:
  an abrasive first powder for polishing hard dental tissue;
  a second powder of a gelling agent; and
  a third powder of a dental treatment agent.

The term "hard dental tissue" is used to cover enamel, dentine, and cement.

The composition of the invention is remarkable in that it serves firstly to perform air polishing treatment of hard dental tissue, and secondly, because of the presence of the gelling second powder, to form an active gel containing the treatment agent and enabling prolonged action to be performed on the treated tooth, in particular therapeutic action. More precisely, and as described in greater detail below, the composition of the invention, when sprayed by the air polisher at a relatively short distance from the treated tissue, serves to perform the desired polishing, and when the air polisher is moved further away from the treated tooth, it serves to form the active gel. Thus, by means of the composition of the invention, it is possible with a single composition and a single air polishing tool to perform two successive actions, the first being polishing hard dental tissue and the second being treating dental tissue with a treatment agent present in the active gel that is formed. The active gel that is formed can serve to treat hard dental tissue and/or soft dental tissue. The formation of the active gel is advantageous to enable the dental treatment agent to act over a relatively long duration. The composition of the invention thus advantageously makes it possible to functionalize conventional dental air polishing treatments to a greater extent by associating it with any type of dental treatment that can be performed by depositing gel, but without that making the treatment more complex or lengthening the time required for the treatment.

The gelling agent may be an organic compound. In a variant, the gelling agent may be an inorganic compound.

In an embodiment, the gelling agent may be selected from: poloxamers, carbomers, polyvinylpyrrolidones, polyethylene glycol, polyvinyl alcohol, seaweed extract, fruit extracts, gelatin, plant seed gums, plant exudates, cellulose or cellulose derivatives, microorganism exudates, fatty acid esters of polyoxyethylene, fatty acid esters of polyoxyethylenesorbitan, clays, and mixtures thereof.

The poloxamer type gelling agent may be a copolymer having polyethylene glycol (PEG)-polypropylene glycol (PPG)-polyethylene glycol blocks.

By way of example, the gelling agent of the seaweed extract type may be selected from: agar-agar, carrageenans, alginates, alginic acid, or furcellerans. By way of example, the alginate type gelling agent may be selected from: sodium alginate, potassium alginate, ammonium alginate, calcium alginate, or propane-1,2-diol alginate.

By way of example, the fruit extract type gelling agent may be pectin.

By way of example, the plant seed gum type gelling agent may be selected from: carob gum, guar gum, or oat gum.

By way of example, the plant exudate type gelling agent may be selected from: gum arabic, karaya gum, or gum tragacanth.

By way of example, the cellulose derivative type gelling agent may be selected from: methyl cellulose, ethyl cellulose, hydroxpyropyl cellulose, hydroxypropylmethyl cellulose, methylethyl cellulose, or carboxymethyl cellulose.

By way of example, the microorganism exudate type gelling agent may be selected from: xanthan gum or gellan gum.

By way of example, the fatty acid ester of polyoxyethylene type gelling agent may be polyoxyethylene stearate.

By way of example, the fatty acid ester of polyoxyethylenesorbitan type gelling agent may be selected from: polyoxyethylene-20-sorbitan monolaurate, polyoxyethylene-20-sorbitan monooleate, polyoxyethylene-20-sorbitan monopalmitate, polyoxyethylene-20-sorbitan monostearate, or polyoxyethylene-20-sorbitan tristearate.

By way of example, the clay type gelling agent may be selected from: kaolin, magnesium aluminosilicates, bentonites, or hectorite.

Preferably, the gelling agent is selected from: poloxamers, hydroxypropylmethyl cellulose, carrageenans, and mixtures thereof.

In an embodiment, the second powder may be present in the composition at a content by weight lying in the range 0.5% to 80%, e.g. in the range 0.5% to 50%.

In an embodiment, the mean size of the grains of the second powder may lie in the range 0.5 micrometers ($\mu$m) to 400 $\mu$m.

Unless specified to the contrary, the term "mean size" is used to designate the dimension given by the half population statistical grain size distribution, known as D50.

The abrasive particles of the first powder may present hardness on the Mohs scale greater than or equal to 1, preferably lying in the range 1 to 5, more preferably in the range 1 to 3.

In an embodiment, the first powder may comprise sodium bicarbonate, calcium carbonate, glycine, a silicate, silica, silicon hydroxide, silicon carbide, powdered pumice stone, diamond powder, aluminum oxide, aluminum hydroxide, or a mixture of these compounds.

The first powder may be a powder of organic particles, which particles may be water-soluble. Preferably, the first powder may comprise sodium bicarbonate, calcium carbonate, glycine, or a mixture of such compounds.

In an embodiment, the first powder may be present in the composition at a content by weight lying in the range 15% to 98%, e.g. in the range 50% to 98%.

In an embodiment, the mean grain size of the first powder may lie in the range 5 µm to 500 µm.

Preferably, the dental treatment agent may be a therapeutic agent.

The therapeutic agent may be an antiseptic agent, an anti-inflammatory agent, an anesthetic agent, a desensitizing agent, a remineralizing agent, an astringent agent, or a mixture of such agents.

Preferably, the desensitizing agent may be selected from sodium fluoride, potassium nitrate, oxalic acid, tin fluoride, or mixtures thereof.

Preferably, the remineralizing agent may be selected from calcium phosphate, calcium chloride, calcium nitrate, sodium phosphate, tricalcium phosphate, tricalcium silicate, hydroxyapatite, silicate glasses, or mixtures thereof.

Preferably, the antiseptic agent may be selected from chlorhexidine chlorhydrate, chlorhexidine dichlorhydrate, chlorhexidine gluconate, chlorhexidine digluconate, sodium hypochlorite, quaternary ammoniums, iodine derivatives, and mixtures thereof.

Preferably, the anti-inflammatory agent may be selected from butoforme, prednisolone acetate, □-glycrrhetinic acid, a non-steroidal anti-inflammatory agent, and mixtures thereof.

Preferably, the anesthetic agent may be selected from lidocaine chlorhydrate.

Preferably, the astringent agent may be selected from aluminum chloride.

In a variant, the dental treatment agent may be a coloring agent, e.g. a fluorescent coloring agent. By way of example, the coloring agent may be an optical whitener. By way of example, the dental treatment agent may thus be selected from sodium fluorescein, brilliant blue, and mixtures thereof.

By way of example, the third powder may present a mean grain size lying in the range 0.5 µm to 500 µm, e.g. lying in the range 0.5 µm to 200 µm.

Advantageously, the composition may further comprise an anti-caking agent. By way of example, the anti-caking agent may be selected from anhydrous colloidal silica, hydrophobic pyrogenic silica, tricalcium phosphate, and mixtures thereof. The anti-caking agent may be in the form of a powder, with the grains of this powder presenting a mean grain size lying in the range 0.5 µm to 200 µm, for example.

Preferably, the composition may comprise:
the first powder at a content by weight lying in the range 15% to 98%;
the second powder at a content by weight lying in the range 0.5% to 80%;
the third powder at a content by weight lying in the range 0.005% to 25%, e.g. lying in the range 0.005% to 20%; and
an anti-caking agent at a content by weight lying in the range 0.05% to 10%.

In an embodiment, the composition may comprise:
the first powder at a content by weight lying in the range 70% to 98%;
the second powder at a content by weight lying in the range 0.5% to 20%;
the third powder at a content by weight lying in the range 0.005% to 25%, e.g. in the range 0.005% to 20%; and
an anti-caking agent at a content by weight lying in the range 0.05% to 10%.

Such a formulation example is particularly suitable for supragingival treatment.

The composition may comprise:
the first powder at a content by weight lying in the range 15% to 70%;
the second powder at a content by weight lying in the range 20% to 80%; e.g. in the range 40% to 80%;
the third powder at a content by weight lying in the range 0.005% to 25%, e.g. in the range 0.005% to 20%; and
an anti-caking agent at a content by weight lying in the range 0.05% to 10%.

Such a formulation example is particularly suitable for subgingival treatment.

The present invention also provides a dental air polishing tool having a nozzle and a tank containing a composition as described above, the nozzle being configured to spray said composition under pressure surrounded by a jet of liquid.

The present invention also provides a composition as described above in which the treatment agent is a therapeutic agent for use as medication in the therapeutic treatment of dental tissue.

Under such circumstances, the therapeutic treatment may comprise at least:
air polishing hard dental tissue, during which the composition surrounded by a jet of liquid is sprayed under pressure against said tissue through a nozzle of an air polishing tool, the nozzle being situated at a first distance from the treated tooth during air polishing;
after air polishing, placing the nozzle at a second distance from the treated tooth that is greater than the first distance; and
forming an active gel including the therapeutic agent on the treated tooth by spraying the composition surrounded by the liquid jet under pressure through the nozzle positioned in this way at the second distance from the treated tooth.

BRIEF DESCRIPTION OF THE DRAWINGS

Other characteristics and advantages of the invention appear from the following description of particular embodiments of the invention given as non-limiting examples and made with reference to the accompanying drawings, in which.

DETAILED DESCRIPTION OF IMPLEMENTATIONS

Figure 1:
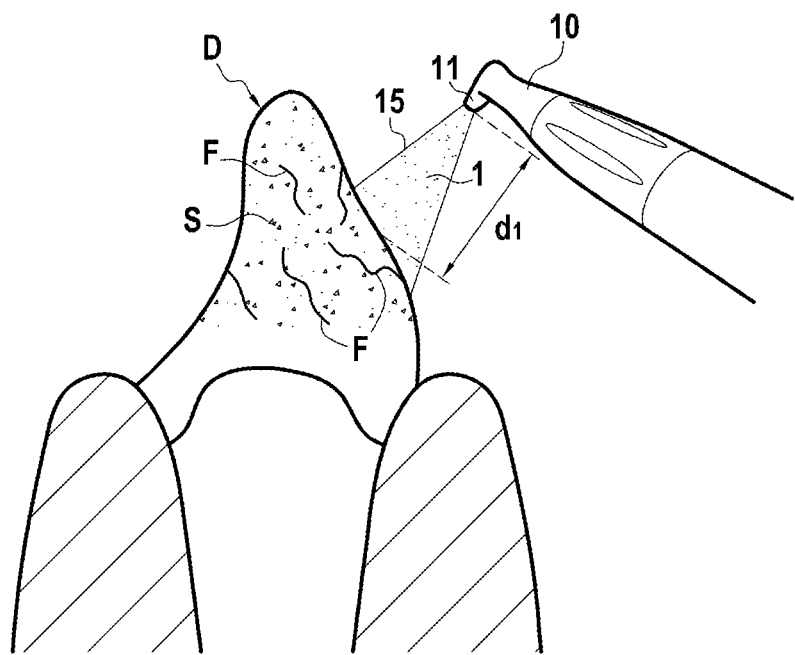
FIGS. 1 and 2 are diagrams showing the conduct of an implementation of the supragingival dental treatment method using a composition of the invention.

FIG. 1 shows the first step of a method of the invention during which a tooth D is subjected to air polishing using a composition of the invention. In the example shown, the tooth D is an incisor. Naturally, it would not go beyond the ambit of the invention to treat some other type of tooth. The tooth D for treatment presents a plurality of cracks F in its surface, which cracks are covered in a deposit of a substance S that is to be removed, such as a deposit of dental plaque.

During this first step, a dental air polishing tool 10 is used to spray the air polishing composition 1 under pressure through the nozzle 11 of the tool 10. More precisely, the jet of composition 1 and a cone 15 of liquid surrounding the jet 1 are sprayed through the nozzle 11. By way of example, the liquid 15 may be water. An example of an air polishing tool 10 suitable for use is the air polisher sold under the reference Air-N-Go□ by the supplier Acetone. As described above, the spray composition 1 comprises at least a mixture of the following three ingredients: a first powder of abrasive particles; a second powder of a gelling agent; and a third powder of the dental treatment agent. The composition 1 may be a powder. The first powder may be different from the second powder. The first powder may be different from the third powder. The second powder may be different from the third powder. In a variant, the second powder and the third powder may be identical. This is possible, for example, when the gelling agent used is a poloxamer, which may have an antiseptic effect and thus constitute simultaneously the gelling agent and the therapeutic agent. As described in detail below, the gelling agent is configured to form a gel on the treated tooth while it is mixing with the liquid sprayed by the air polishing tool 10. Advantageously, the composition 1 may also comprise an anti-caking agent, as described above.

The impact of the spray composition 1 against the tooth D serves to clean the surface of the tooth D and to eliminate the deposit S. During this first step, the nozzle 11 is situated at a relatively short distance $d_1$ from the tooth D for treatment. As a result, the jet of composition 1 impacts against the tooth T with relatively high pressure, thereby eliminating the deposit S present on the tooth D. By way of example, the distance $d_1$ is less than or equal to 0.5 centimeters (cm).

Furthermore, during the final step and still because of this high pressure, the ingredients of the composition 1 do not become deposited on the tooth D for more than a few seconds, and they are removed from the surface of the tooth D together with the substance S immediately after impact. By way of example, the treatment of a tooth during this first step may last for at least one second, and may last for three seconds, by way of example. Advantageously, the first powder may comprise at least one of the following compounds: sodium bicarbonate, calcium carbonate, glycine, a silicate, silica, silicon hydroxide, silicon carbide, powdered pumice stone, diamond powder, aluminum oxide, aluminum hydroxide, or a mixture of these compounds. Advantageously, the first powder may comprise at least one of the following compounds: sodium bicarbonate, calcium carbonate, glycine, or a mixture of such compounds.

Figure 2:
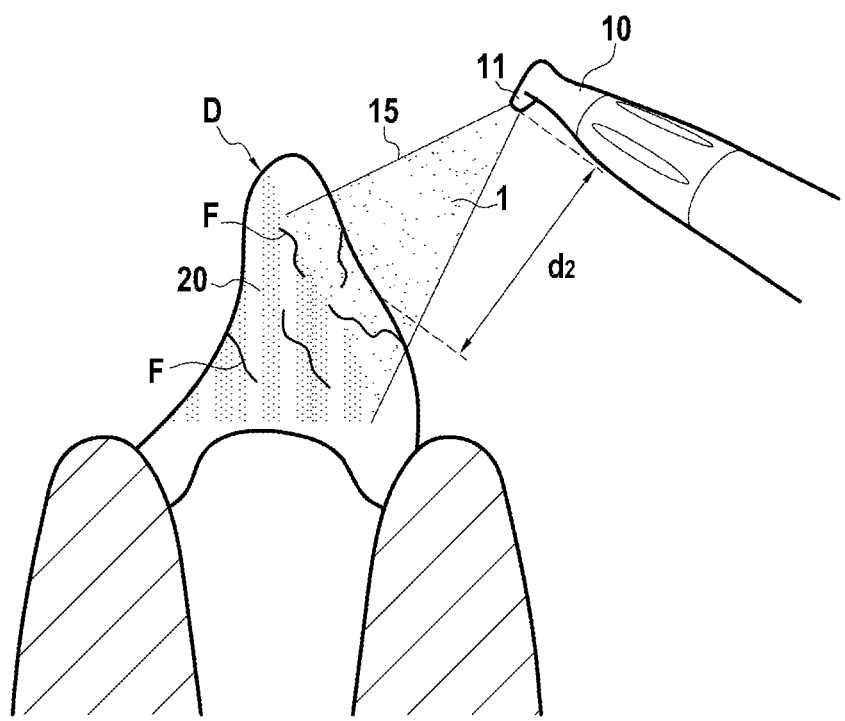

Once the polishing step has been performed, the user moves the nozzle 11 a little away from the tooth D that has been cleaned in this way in order to position it at a distance $d_2$ and form an active gel 20 on the tooth D. In the example shown in FIGS. 1 to 3, the treated portion of the tooth is situated above the gum: this is a supragingival dental treatment method. By way of example, the distance $d_2$ is greater than or equal to 0.6 cm, e.g. 1 cm. The performance of this step is shown in FIG. 2. The active gel 20 is formed as a result of mixing between the second powder and the water sprayed by the tool 10. This gel 20 forms only when the nozzle 11 is relatively far away from the tooth D, since the impact pressure of the composition 1 sprayed against the tooth D is then reduced, thereby enabling the ingredients of the composition 1 to become deposited on the tooth D and enabling the gelling agent to form the gel by mixing with the liquid. Advantageously, the gelling agent may be selected from: poloxamers, hydroxypropylmethyl cellulose, methyl cellulose, carrageenans, and mixtures thereof. The active gel 20 that is formed contains the dental treatment agent initially present in the composition 1. The dental treatment agent may be a therapeutic agent as described above. The active gel 20 serves to fill the cracks F present in the surface of the tooth D and to perform dental treatment over a relatively long duration, e.g. at least one minute, e.g. several minutes. The active gel 20 can thus make it possible to perform at least one of the following actions: remineralization, desensitization, or disinfection of the treated dental tissue. The active gel 20 is configured to remain in contact with the tooth D in order to perform the looked-for dental treatment. Advantageously, the active gel 20 may be water-soluble in order to dissolve progressively in the patient's mouth once the dental treatment has been performed.

Figure 3:
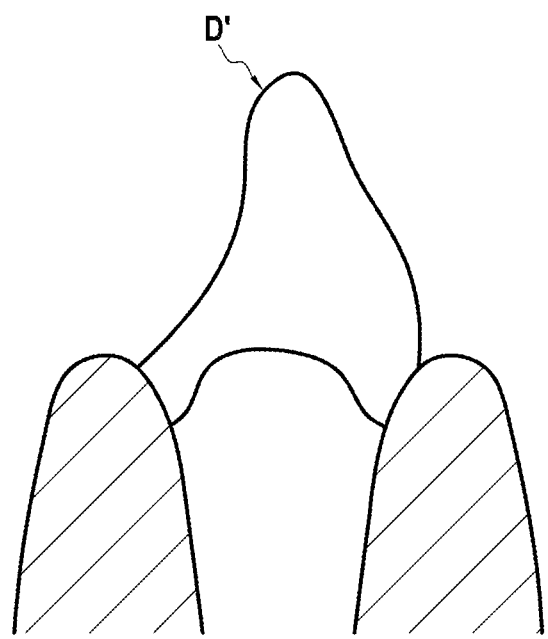
FIG. 3 shows a tooth treated by the method shown in FIGS. 1 and 2.

The treated tooth D' as obtained after the first and second steps is shown in FIG. 3. The cracks F that were initially present in the non-treated tooth D may be filled as a result of the treatment of the invention, as shown.

Figure 4:
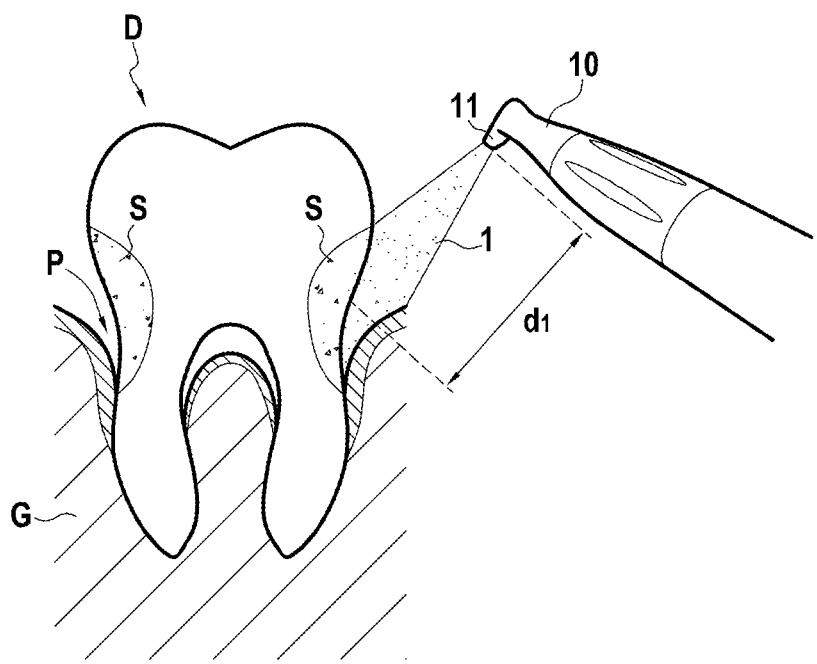
FIGS. 4 and 5 are diagrams showing the conduct of an implementation of the subgingival treatment method using a composition of the invention.
Figure 5:
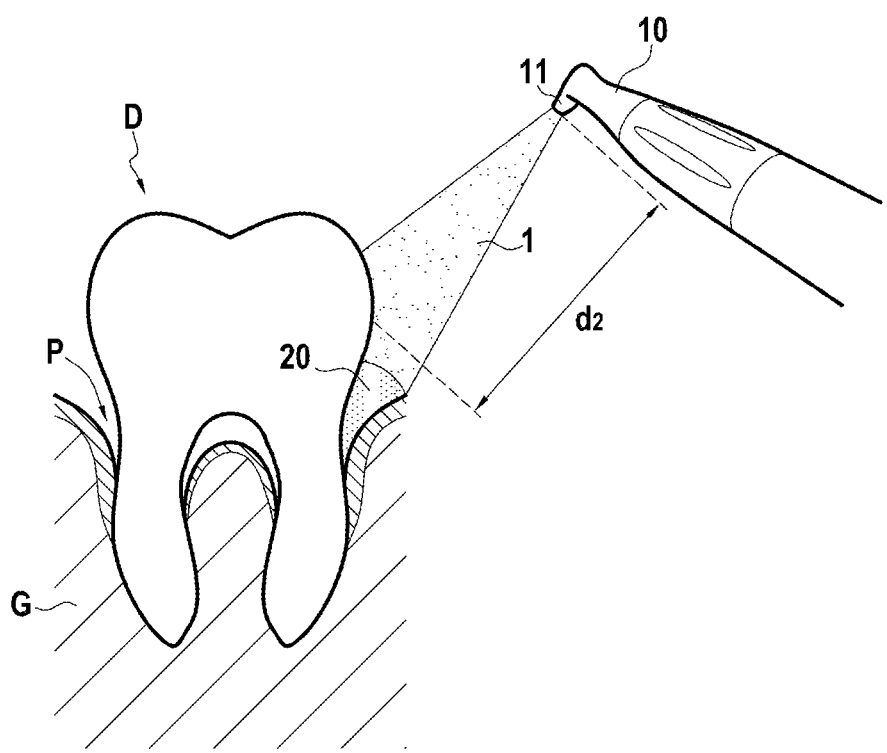
Figure 6:
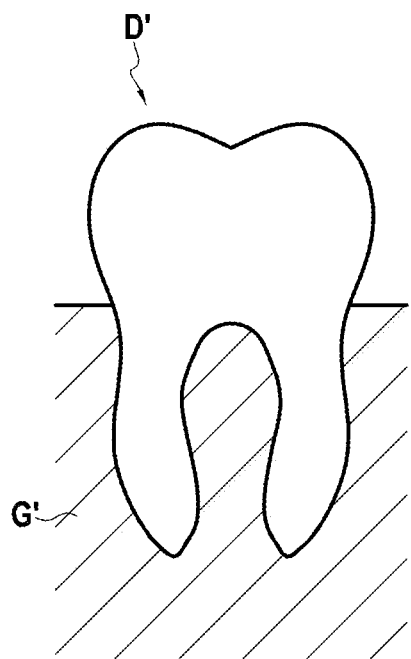
FIG. 6 shows a tooth treated by the method shown in FIGS. 4 and 5.

FIGS. 4 to 6 show the treatment of a tooth D suffering from periodontitis. This tooth D is a molar in the example shown. Air polishing is initially performed using the tool 10 with a composition as described above in order to eliminate the substance S present at the surface of the tooth D (see FIG. 4). Once cleaning has been done, the nozzle 11 is then moved further away from the treated tooth in order to form an active gel 20 thereon (see FIG. 5). The active gel 20 is formed in particular in the periodontal pocket P present between the retracted gum G and the tooth D. The treatment that is performed serves to treat the periodontitis and enables the gum to restore itself. The gel 20 that is formed may also include a remineralizing agent in order to restore the enamel of the treated tooth. After treatment, a healthy gum G' is obtained supporting the treated tooth D'. For this type of subgingival treatment, it is advantageously possible to use a composition presenting a large quantity of abrasive particles of weak abrasive power or a small quantity of abrasive having strong abrasive power.

EXAMPLES

In the examples, all of the proportions are expressed as percentages by weight, unless specified to the contrary, temperature is measured in degrees Celsius (° C.), and pressure is taken to be equal to atmospheric pressure (1 bar), unless specified to the contrary.

Example 1

An air polishing composition was made having the composition set out in Table 1 below.

TABLE 1

| Formulation | % |
| --- | --- |
| Sodium bicarbonate | 81.50 |
| Aerosil R972 | 4.00 |
| Sodium saccharin | 2.00 |
| Sodium fluoride | 0.50 |
| Potassium nitrate | 2.50 |
| Calcium nitrate tetrahydrate | 2.00 |
| Sodium hydrogen phosphate dodecahydrate | 2.5 |
| Poloxamer | 5.00 |

The composition was prepared in the manner described below.

A first pre-mixture A was made by adding half of the quantity of sodium bicarbonate and half of the quantity of Aerosil R972 to a mixture comprising the calcium nitrate tetrahydrate and the sodium hydrogen phosphate dodecahydrate. The mixture was homogenized using a cube mixer sold under the trademark Frogerais. The mixture was then screened at 200 µm using a vibrating screen.

A second pre-mixture B was made by mixing the other half of the quantity of sodium bicarbonate, the other half of the quantity of Aerosil R972, the sodium saccharin, the sodium fluoride, the potassium nitrate, and the poloxamer. The mixture was homogenized using a cube mixer sold under the trademark Frogerais. The mixture was then screened at 200 µm with a vibrating screen.

The pre-mixtures A and B were then homogenized in order to obtain the composition set out in Table 1 above.

The composition as obtained in this way was then fragmented and screened at 200 µm respectively using a hammer mill sold by the supplier Poitemill Forplex and by a vibrating screen.

The resulting powder composition for air polishing presented good dry flow and a D50 mean grain size lying in the range 70 µm to 90 µm when measured with a laser granulometer type instrument sold by the supplier Malvern.

Figure 7:
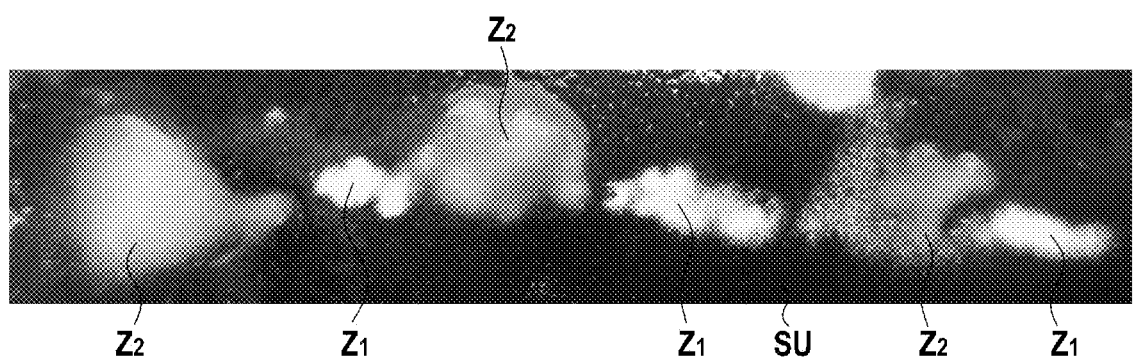
FIG. 7 is a photograph of a substrate treated by an example of a composition of the invention showing both the polishing that is performed and also the formation of the gel.

When incorporated in a dental air polishing tool, the composition serves firstly to perform supragingival polishing and then, by moving away the nozzle of the air polishing tool, to form a remineralizing and desensitizing gel on the treated tooth. In this respect, FIG. 7 is a photograph of a card substrate SU coated in a layer of black paint onto which the composition of Example 1 was sprayed by a dental air polishing tool. The zones $Z_1$ correspond to zones that were "treated" at short range. These zones $Z_1$ were polished without forming gel. It can be seen that after the polishing formed in the zones $Z_1$, the coating of black paint was eliminated, thereby revealing the underlying substrate, which appears white in the photograph of FIG. 7. The zones $Z_2$ correspond to zones that were initially polished, like the zones $Z_1$, and for which the nozzle of the air polishing tool was then moved away so as to form a gel. These zones $Z_2$ appear gray in the photograph of FIG. 7 because of the formation of the gel.

Example 2

An air polishing composition was fabricated having the formulation set out in Table 2 below.

TABLE 2

| Formulation | % |
| --- | --- |
| Calcium carbonate | 20.00 |
| Aerosil R972 | 1.00 |
| Sodium saccharin | 1.00 |
| Chlorhexidine chlorhydrate | 2.50 |
| Potassium nitrate | 2.50 |
| □-tricalcium phosphate | 17.00 |
| Carrageenan | 56.00 |

The composition set out in Table 2 above was obtained by adding the following to the calcium carbonate and in this order: sodium saccharin, chlorhexidine chlorhydrate, potassium nitrate, □-tricalcium phosphate, carrageenan gelling agent, and Aerosil R972.

The mixture was then homogenized using a mixer of the bin blender type sold by the supplier Servolift. The resulting composition was then screened with a vibrating screen.

The resulting composition presented mean grain size in the range 40 µm to 60 µm when measured using a "Mastersizer 2000" type laser granulometer sold by the supplier Malvern.

The composition fabricated in that way is suitable for supragingival or subgingival use for polishing and then forming a gel constituting an antiseptic "dressing" for treating the periodontal pocket.

Example 3

An air polishing composition was fabricated having the formulation set out in Table 3 below.

TABLE 3

| Formulation | % |
| --- | --- |
| Glycine | 60.00 |
| Aerosil R972 | 2.00 |
| Sodium saccharin | 2.00 |
| Mint flavoring | 0.50 |
| Lidocaine chlorhydrate | 2.50 |
| Hydroxapatite | 18.00 |
| Methocel E4M | 15.00 |

This composition was fabricated by milling the glycine with a hammer mill sold by the supplier Poitemill Forplex. Thereafter the following were added to the milled glycine and in this order: sodium saccharin, essential oil of peppermint, lidocaine chlorhydrate, hydroxapatite, Methocel E4M, and Aerosil R972. The composition was homogenized using a V mixer sold by the supplier Olsa and then screened at 300 µm with a vibrating screen.

The resulting composition presented mean grain size lying in the range 15 µm to 35 µm as measured with a "Mastersizer 2000" type laser granulometer sold by the supplier Malvern.

The composition as fabricated in that way can be used, after forming the active gel, to anesthetize soft dental tissue when applied in a periodontal pocket while cleaning the pocket.

Example 4

An air polishing composition was fabricated having the formulation set out in Table 4 below.

TABLE 4

| Formulation | % |
| --- | --- |
| Glycine | 15.00 |
| Aerosil R972 | 3.00 |
| Sodium saccharin | 2.00 |
| Aluminum chloride | 10.00 |
| Kaolin | 27.70 |
| Essential oil of lemon | 0.30 |
| Methyl cellulose | 42.00 |

A pre-mixture A was made by adding half of the quantity of glycine and half of the quantity of Aerosil R972 to the mixture of aluminum chloride and kaolin. The mixture was homogenized using a cube mixer sold under the trademark Frogerais and then screened at 200 µm with a vibrating screen.

A second pre-mixture B was made by mixing the other half of the quantity of glycine, the sodium saccharin, the essential oil of lemon, the methyl cellulose, and the other half of the quantity of Aerosil R972. The mixture was homogenized using a cube mixer sold by the supplier Servolift and then screened at 200 μm using an oscillating grinder having the trademark Frewitt.

Thereafter, the pre-mixture A and the pre-mixture B were homogenized. The resulting composition was then fragmented and screened at 200 μm using a cone mill sold by Frewitt in order to obtain the composition set out in Table 4 above. The composition represented good dry flow and D50 mean grain size lying in the range 25 μm to 45 μm as measured with a laser granulometer type instrument sold by the supplier Malvern.

The composition as fabricated in that way can be used to perform subgingival polishing and subsequently, by moving away the nozzle of the air polisher, to form a hemostatic gel serving to keep the sulcus open after rinsing the gel because of the treatment by aluminum chloride.

The term "lying in the range . . . to . . . " should be understood as including the bounds.

The invention claimed is:

1. A method of treating dental tissue using a composition for air polishing a surface of hard dental tissue, the composition comprising at least:
    an abrasive first powder suitable for polishing hard dental tissue, the first powder comprising sodium bicarbonate, calcium carbonate, glycine, a silicate, silica, silicon hydroxide, silicon carbide, powdered pumice stone, diamond powder, aluminum oxide, aluminum hydroxide, or a mixture of these compounds, a mean grain size of the first powder being in the range of 5 μm to 500 μm;
    a second powder of a gelling agent comprising a poloxamer, hydroxypropylmethyl cellulose, methyl cellulose, a carrageenan, or a mixture thereof; and
    a third powder of a dental treatment agent, the dental treatment agent comprising a therapeutic agent, a coloring agent, or a mixture thereof;
    wherein the method comprises at least:
    air polishing the hard dental tissue during which the composition is sprayed against said tissue at a first distance from the tissue;
    and then spraying the composition at a second distance from the tissue, the second distance being greater than the first distance, to form a gel on the hard dental tissue and/or on soft dental tissue.

2. The method according to claim 1, the second powder being present in the composition at a content by weight lying in a range of 0.5% to 80%.

3. The method according to claim 1, a mean size of the grains of the second powder lying in a range of 0.5 μm to 400 μm.

4. The method according to claim 1, the first powder comprising sodium bicarbonate, calcium carbonate, glycine, or a mixture of such compounds.

5. The method according to claim 1, the first powder comprising glycine and the second powder comprising a poloxamer.

6. The method according to claim 1, the first powder comprising sodium bicarbonate and the second powder comprising a poloxamer.

7. The method according to claim 1, the first powder being present in the composition at a content by weight lying in a range of 15% to 98%.

8. The method according to claim 1, the composition comprising:
    the first powder at a content by weight lying in a range 15% to 98%;
    the second powder at a content by weight lying in a range 0.5% to 80%; and
    the third powder at a content by weight lying in a range 0.005% to 25%; and
    optionally, an anti-caking agent at a content by weight lying in a range 0.05% to 10%.

9. The method according to claim 8, the composition comprising:
    the first powder at a content by weight lying in the range of 70% to 98%;
    the second powder at a content by weight lying in the range of 0.5% to 20%; and
    the third powder at a content by weight lying in the range of 0.005% to 25%; and
    optionally, an anti-caking agent at a content by weight lying in the range of 0.05% to 10%.

10. The method according to claim 8, the composition comprising:
    the first powder at a content by weight lying in the range of 15% to 70%;
    the second powder at a content by weight lying in the range of 20% to 80%; and
    the third powder at a content by weight lying in the range of 0.005% to 25%; and
    optionally, an anti-caking agent at a content by weight lying in the range of 0.05% to 10%.

11. The method according to claim 1, the therapeutic agent comprising an antiseptic agent, an anti-inflammatory agent, an anesthetic agent, a desensitizing agent, a remineralizing agent, an astringent agent, or a mixture of such agents.

12. The method according to claim 1, wherein the composition is sprayed by a dental air polishing tool having a nozzle and a tank containing the composition, the composition being prayed through the nozzle under pressure surrounded by a jet of liquid.

13. The method according to claim 1, wherein the treatment is a therapeutic treatment of dental tissue.

* * * * *